(12) United States Patent
Zuo et al.

(10) Patent No.: US 10,371,690 B2
(45) Date of Patent: Aug. 6, 2019

(54) METHODS AND SYSTEMS FOR CORRECTION OF OIL-BASED MUD FILTRATE CONTAMINATION ON SATURATION PRESSURE

(71) Applicant: Schlumberger Technology Corporation, Sugar Land, TX (US)

(72) Inventors: Youxiang Zuo, Burnaby (CA); Christopher Harrison, Auburndale, MA (US); Adriaan Gisolf, Houston, TX (US); Cosan Ayan, Istanbul (TR); Michael Mallari Toribio, Tokyo (JP); Chetankumar Natwarlal Desai, Saint Cloud (FR); Oliver Clinton Mullins, Houston, TX (US); Matthew T. Sullivan, Westwood, MA (US); Elizabeth Smythe, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 730 days.

(21) Appl. No.: 14/535,199

(22) Filed: Nov. 6, 2014

(65) Prior Publication Data
US 2016/0131630 A1    May 12, 2016

(51) Int. Cl.
*G01N 33/28* (2006.01)
*E21B 49/00* (2006.01)
(Continued)

(52) U.S. Cl.
CPC ......... *G01N 33/2823* (2013.01); *E21B 47/00* (2013.01); *E21B 47/06* (2013.01);
(Continued)

(58) Field of Classification Search
None
See application file for complete search history.

(56) References Cited

U.S. PATENT DOCUMENTS

| 4,646,083 A * | 2/1987 | Woods | G01V 11/002 340/855.3 |
| 6,178,815 B1 * | 1/2001 | Felling | E21B 49/10 166/250.07 |

(Continued)

FOREIGN PATENT DOCUMENTS

WO    2010120285 A1    10/2010

OTHER PUBLICATIONS

F.B. Thomas, Deconvolution of Drilling Fluid-Contaminated Oil Samples, 2002, 20 pages.*

(Continued)

*Primary Examiner* — Tung S Lau
(74) *Attorney, Agent, or Firm* — Michael Dae

(57) ABSTRACT

Embodiments of the disclosure can include systems, methods, and devices for determining saturation pressure of an uncontaminated fluid. Downhole saturation pressure measurements and downhole OBM filtrate contamination of a contaminated fluid may be obtained and a relationship may be determined between the saturation pressure measurements and OBM filtrate contamination. The relationship may be extrapolated to zero OBM filtrate contamination to determine the saturation pressure of the uncontaminated fluid. In some embodiments, OBM filtrate contamination may be determined from downhole saturation pressure measurements during pumpout of a fluid.

6 Claims, 10 Drawing Sheets

(51) Int. Cl.

| | | |
|---|---|---|
| *E21B 49/08* | (2006.01) | |
| *G01N 7/00* | (2006.01) | |
| *E21B 47/00* | (2012.01) | |
| *E21B 47/06* | (2012.01) | |
| *G01N 21/31* | (2006.01) | |

(52) U.S. Cl.
  CPC ............ *E21B 49/005* (2013.01); *E21B 49/08* (2013.01); *G01N 7/00* (2013.01); *G01N 21/31* (2013.01)

(56) References Cited

U.S. PATENT DOCUMENTS

| | | | |
|---|---|---|---|
| 6,956,204 | B2 | 10/2005 | Dong et al. |
| 6,994,164 | B2* | 2/2006 | Tare .................. C09K 8/50 166/250.14 |
| 8,024,125 | B2 | 9/2011 | Hsu et al. |
| 2013/0110402 | A1* | 5/2013 | Godager ............ E21B 47/122 702/7 |
| 2013/0311099 | A1* | 11/2013 | Eyuboglu ............ E21B 49/08 702/11 |
| 2013/0340518 | A1* | 12/2013 | Jones ................. E21B 49/005 73/152.55 |
| 2014/0116071 | A1* | 5/2014 | Jung .................. E21B 47/011 62/56 |
| 2014/0316705 | A1 | 10/2014 | Zuo et al. |
| 2015/0142317 | A1* | 5/2015 | Zuo .................... E21B 49/088 702/6 |

OTHER PUBLICATIONS

Mahmood Amani, Comparative Study of Using Oil-Based Mud Versus Water-Based Mud in HPHT Fields, vol. 4, No. 2, 2012, pp. 18-27.*
Definition of "Uncontaminated", Nov. 30, 2018, 1 page.*
International Search Report and Written Opinion issued in related PCT application PCT/US2015/056698 dated Feb. 9 2016, 13 pages.
Austad, et al. "Compositional and PVT Properties of Reservoir Fluids Contaminated by Drilling Fluid Filtrate", Journal of Petroleum Science and Engineering, 20, 213-244 (2001).
O'Keefe, et al. "Focused Sampling of Reservoir Fluids Achieves Undetectable Levels of Contamination," SPE 101084, SPE Asia Pacific Oil & Gas Conference and Exhibition, Adelaide, Australia, Sep. 11-13, 2006, pp. 1-20.
Gozalpour, et al. "Predicting Reservoir Fluid Phase and Volumetric Behavior From Samples Contaminated with Oil-Based Mud", SPE Reservoir Evaluation & Engineering, Jun. 2002, pp. 197-205.
Hy-Billiot, et al. "Getting the Best from Formation Tester Sampling", SPE 77771, SPE ATCE, San Antonio, Texas, Sep. 29-Oct. 2, 2002, pp. 1-9.
MacMillan, et al. "How to Obtain Reservoir Fluid Properties from an Oil Sample Contaminated with Synthetic Drilling Mud," SPE 38852, SPE ATCE, San Antonio, TX, Oct. 5-8, 1997, pp. 113-123.
U.S. Appl. No. 14/085,550, filed Nov. 20, 2013.
U.S. Appl. No. 14/085,589, filed Nov. 20, 2013.
U.S. Appl. No. 14/177,744, filed Feb. 11, 2014.
International Preliminary Report on Patentability issued in the related PCT application PCT/US2015/056698, dated May 5, 2017 (8 pages).

* cited by examiner

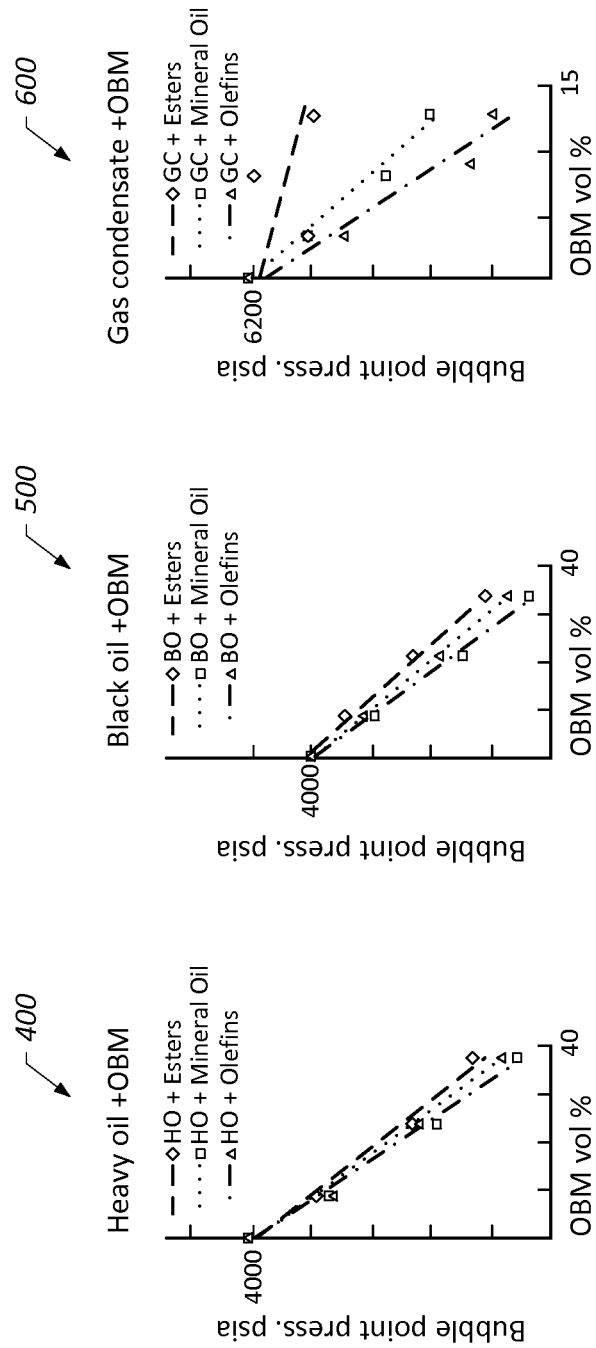

METHODS AND SYSTEMS FOR CORRECTION OF OIL-BASED MUD FILTRATE CONTAMINATION ON SATURATION PRESSURE

FIELD OF THE DISCLOSURE

This disclosure relates to downhole fluid monitoring, and, more particularly to methods and systems for correction of oil-based mud filtrate contamination on saturation pressure.

BACKGROUND

This disclosure relates to determination of fluid properties using downhole fluid analysis (DFA). Fluid properties like gas-oil ratio (GOR), density, optical density (OD), composition, and others may be measured, detected, and/or estimated for fluids downhole in a well. Oil-based drilling mud (OBM) filtrate contamination may affect the fluid properties measured downhole, and obtaining fluid samples having zero OBM filtrate contamination may be difficult. The accuracy of such fluid properties may affect reservoir development, production, and management.

SUMMARY

A summary of certain embodiments disclosed herein is set forth below.

It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of this disclosure relate to various methods and systems for correction of oil-based mud filtrate contamination on saturation pressure. In particular, certain embodiments of the disclosure can include methods and systems for determining saturation pressure of an uncontaminated fluid. According to some embodiments, a method is provided that can include obtaining, by using at least one property of a contaminated fluid measured downhole by a downhole tool, oil-based mud (OBM) filtrate contamination of the contaminated fluid. The contaminated fluid includes uncontaminated fluid and the OBM filtrate. The method can further include obtaining downhole saturation pressure measurements of the reservoir fluid and determining a relationship between the downhole saturation pressure measurements and the OBM filtrate contamination. The method can also include extrapolating the determined relationship between the downhole saturation pressure measurements and the OBM filtrate contamination to a zero OBM filtrate contamination and determining a saturation pressure of the uncontaminated fluid at the zero OBM filtrate contamination.

According to another embodiment, a system is provided that can include a downhole tool operable within a wellbore extending into a subterranean formation, a controller coupled to the downhole tool, and a non-transitory tangible machine-readable memory coupled to a processor of the controller. The non-transitory tangible machine-readable memory stores machine-readable instructions that when executed by the processor cause the processor to perform operations that can include obtaining, by using at least one property of a contaminated fluid measured downhole by a downhole tool, oil-based mud (OBM) filtrate contamination of the contaminated fluid. The contaminated fluid can include uncontaminated fluid and the OBM filtrate. Additionally, the non-transitory tangible machine-readable memory stores machine-readable instructions that when executed by the processor cause the processor to perform operations that can further include obtaining downhole saturation pressure measurements of the reservoir fluid and determining a relationship between the downhole saturation pressure measurements and the OBM filtrate contamination. The non-transitory tangible machine-readable memory also stores machine-readable instructions that when executed by the processor cause the processor to perform operations that can include extrapolating the determined relationship between the downhole saturation pressure measurements and the OBM filtrate contamination to a zero OBM filtrate contamination and determining a saturation pressure of the uncontaminated fluid at the zero OBM filtrate contamination.

Further, embodiments of this disclosure relate to various methods and systems for determining OBM filtrate contamination of a contaminated fluid. According to some embodiments, a method is provided that can include measuring downhole saturation pressures of a contaminated fluid over a pumpout volume or a pumpout time, the contaminated fluid including uncontaminated fluid and an OBM filtrate. The method can further include determining a function for the measured saturation pressures based on the pumpout volume or pumpout time and extrapolating the function to infinite pumpout volume or infinite pumpout time. Additionally, the method can include determining a saturation pressure for the uncontaminated fluid at the infinite pumping volume or infinite pumping time and obtaining a saturation pressure of the OBM filtrate. The method can also include determining an OBM filtrate contamination of the contaminated fluid based on the saturation pressure for the uncontaminated fluid, the saturation pressure for the OBM filtrate, and the measured saturation pressure for the contaminated fluid.

According to another embodiments, a system is provided that includes a downhole tool operable within a wellbore extending into a subterranean formation, a controller coupled to the downhole tool, and a non-transitory tangible machine-readable memory coupled to a processor of the controller. The non-transitory tangible machine-readable memory stores machine-readable instructions that when executed by the processor cause the processor to perform operations that can include measuring downhole saturation pressures of a contaminated fluid over a pumpout volume or a pumpout time, the contaminated fluid including uncontaminated fluid and an OBM filtrate. Additionally, the non-transitory tangible machine-readable memory stores machine-readable instructions that when executed by the processor cause the processor to perform operations that can further include further includes determining a function for the measured saturation pressures based on the pumpout volume or pumpout time and extrapolating the function to infinite pumpout volume or infinite pumpout time. The non-transitory tangible machine-readable memory stores machine-readable instructions that when executed by the processor cause the processor to perform operations that can further include determining a saturation pressure for the uncontaminated fluid at the infinite pumping volume or infinite pumping time and obtaining a saturation pressure of the OBM filtrate. Further, the non-transitory tangible machine-readable memory stores machine-readable instructions that when executed by the processor cause the processor to perform operations that can further include determining an OBM filtrate contamination of the contaminated fluid based on the saturation pressure for the uncontaminated fluid, the saturation pressure for the OBM filtrate, and the measured saturation pressure for the contaminated fluid.

Various refinements of the features noted above may be undertaken in relation to various aspects of the present disclosure. Further features may also be incorporated in these various aspects as well. These refinements and additional features may be determined individually or in any combination. For instance, various features discussed below in relation to the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which:

FIGS. 4-6 are plots of saturation pressure vs. OBM filtrate contamination in accordance with an embodiment of the present disclosure;

DETAILED DESCRIPTION

Described herein are various embodiments related to the determination of saturation pressure of an uncontaminated fluid using downhole saturation pressure measurements of a contaminated fluid and OBM filtrate contamination. As used herein, the saturation pressure may refer to a dew point pressure or a bubble point pressure. In some embodiments, downhole OBM filtrate contamination and downhole saturation pressure measurements of a contaminated fluid may be obtained. In some embodiments, a regression (e.g., a linear regression) may be performed on a plot of downhole saturation pressure measurements vs. OBM filtrate contamination to determine a linear function. The function (e.g., a linear function) may be extrapolated to zero OBM filtrate contamination to determine the saturation pressure (bubble point pressure or dew point pressure) of the uncontaminated fluid.

Also described herein are embodiments related to the determination of OBM filtrate contamination from downhole saturation pressure measurements. In some embodiments, downhole saturation pressure, such as bubble point pressures, may be measured during a pumpout volume or time. A function (e.g., a power function) for the saturation pressure vs. pumpout volume or time may be fitted, and the function may be extrapolated to infinite volume or infinite time to obtain a bubble point pressure for the uncontaminated fluid. The OBM filtrate saturation pressure may also be obtained. The OBM filtrate contamination may be determined using the saturation pressure for the uncontaminated fluid, the saturation pressure for the OBM filtrate, and the measured saturation pressure for the contaminated fluid.

These and other embodiments of the disclosure will be described in more detail through reference to the accompanying drawings in the detailed description of the disclosure that follows. This brief introduction, including section titles and corresponding summaries, is provided for the reader's convenience and is not intended to limit the scope of the claims or the proceeding sections. Furthermore, the techniques described above and below may be implemented in a number of ways and in a number of contexts. Several example implementations and contexts are provided with reference to the following figures, as described below in more detail. However, the following implementations and contexts are but a few of many.

Figure 1:
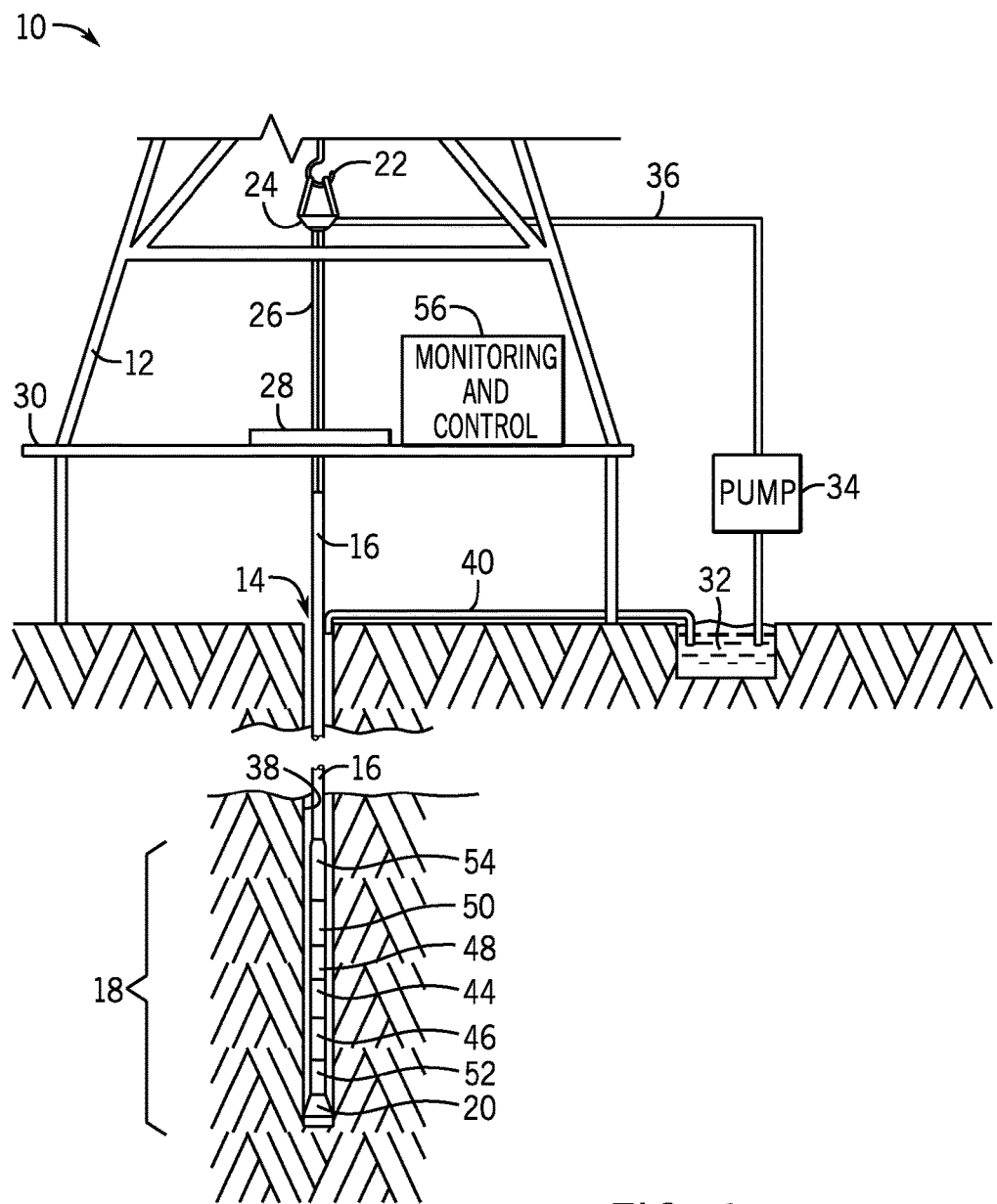
FIG. 1 generally depicts a drilling system having a fluid sampling tool in a drill string in accordance with an embodiment of the present disclosure.

More specifically, a drilling system 10 is depicted in FIG. 1 in accordance with one embodiment. While certain elements of the drilling system 10 are depicted in this figure and generally discussed below, it will be appreciated that the drilling system 10 may include other components in addition to, or in place of, those presently illustrated and discussed. As depicted, the system 10 can include a drilling rig 12 positioned over a well 14. Although depicted as an onshore drilling system 10, it is noted that the drilling system could instead be an offshore drilling system. The drilling rig 12 can support a drill string 16 that includes a bottomhole assembly 18 having a drill bit 20. The drilling rig 12 can rotate the drill string 16 (and its drill bit 20) to drill the well 14.

The drill string 16 can be suspended within the well 14 from a hook 22 of the drilling rig 12 via a swivel 24 and a kelly 26. Although not depicted in FIG. 1, the skilled artisan will appreciate that the hook 22 can be connected to a hoisting system used to raise and lower the drill string 16 within the well 14. As one example, such a hoisting system could include a crown block and a drawworks that cooperate to raise and lower a traveling block (to which the hook 22 is connected) via a hoisting line. The kelly 26 can be coupled to the drill string 16, and the swivel 24 can allow the kelly 26 and the drill string 16 to rotate with respect to the hook 22. In the presently illustrated embodiment, a rotary table 28 on a drill floor 30 of the drilling rig 12 can be constructed to grip and turn the kelly 26 to drive rotation of the drill string 16 to drill the well 14. In other embodiments, however, a top drive system could instead be used to drive rotation of the drill string 16.

During operation, drill cuttings or other debris may collect near the bottom of the well 14. Drilling fluid 32, also referred to as drilling mud, can be circulated through the well 14 to remove this debris. The drilling fluid 32 may also clean and cool the drill bit 20 and provide positive pressure within the well 14 to inhibit formation fluids from entering the wellbore. In FIG. 1, the drilling fluid 32 can be circulated through the well 14 by a pump 34. The drilling fluid 32 can be pumped from a mud pit (or some other reservoir, such as a mud tank) into the drill string 16 through a supply conduit 36, the swivel 24, and the kelly 26. The drilling fluid 32 can exit near the bottom of the drill string 16 (e.g., at the drill bit 20) and can return to the surface through the annulus 38 between the wellbore and the drill string 16. A return conduit 40 can transmit the returning drilling fluid 32 away from the well 14. In some embodiments, the returning drilling fluid 32 can be cleansed (e.g., via one or more shale shakers, desanders, or desilters) and reused in the well 14. The drilling fluid 32 may include an oil-based mud (OBM) that may include synthetic muds, diesel-based muds, or other suitable muds.

In addition to the drill bit 20, the bottomhole assembly 18 can also include various instruments that measure information of interest within the well 14. For example, as depicted in FIG. 1, the bottomhole assembly 18 can include a logging-while-drilling (LWD) module 44 and a measurement-while-drilling (MWD) module 46. Both modules can include sensors, housed in drill collars, that can collect data and enable the creation of measurement logs in real-time during a drilling operation. The modules could also include memory devices for storing the measured data. The LWD module 44 can include sensors that measure various characteristics of the rock and formation fluid properties within the well 14. Data collected by the LWD module 44 could include measurements of gamma rays, resistivity, neutron porosity, formation density, sound waves, optical density, and the like. The MWD module 46 can include sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 can be used to control drilling operations. The bottomhole assembly 18 can also include one or more additional modules 48, which could be LWD modules, MWD modules, or some other modules. It is noted that the bottomhole assembly 18 is modular, and that the positions and presence of particular modules of the assembly could be changed as desired. Further, as discussed in detail below, one or more of the modules 44, 46, and 48 can be or can include a fluid sampling tool configured to obtain a sample of a fluid from a subterranean formation and perform downhole fluid analysis to measure various properties of the sampled fluid. These properties may include an estimated density and/or optical density of the OBM filtrate, the sampled fluid, and other fluids. These and other estimated properties may be determined within or communicated to the LWD module 44, such as for subsequent utilization as input to various control functions and/or data logs.

The bottomhole assembly 18 can also include other modules. As depicted in FIG. 1 by way of example, such other modules can include a power module 50, a steering module 52, and a communication module 54. In one embodiment, the power module 50 can include a generator (such as a turbine) driven by flow of drilling mud through the drill string 16. In other embodiments, the power module 50 could also or instead include other forms of power storage or generation, such as batteries or fuel cells. The steering module 52 may include a rotary-steerable system that facilitates directional drilling of the well 14. The communication module 54 can enable communication of data (e.g., data collected by the LWD module 44 and the MWD module 46) between the bottomhole assembly 18 and the surface. In one embodiment, the communication module 54 can communicate via mud pulse telemetry, in which the communication module 54 uses the drilling fluid 32 in the drill string as a propagation medium for a pressure wave encoding the data to be transmitted.

The drilling system 10 can also include a monitoring and control system 56. The monitoring and control system 56 can include one or more computer systems that enable monitoring and control of various components of the drilling system 10. The monitoring and control system 56 can also receive data from the bottomhole assembly 18 (e.g., data from the LWD module 44, the MWD module 46, and the additional module 48) for processing and for communication to an operator, to name just two examples. While depicted on the drill floor 30 in FIG. 1, it is noted that the monitoring and control system 56 could be positioned elsewhere, and that the system 56 could be a distributed system with elements provided at different places near or remote from the well 14.

Figure 2:
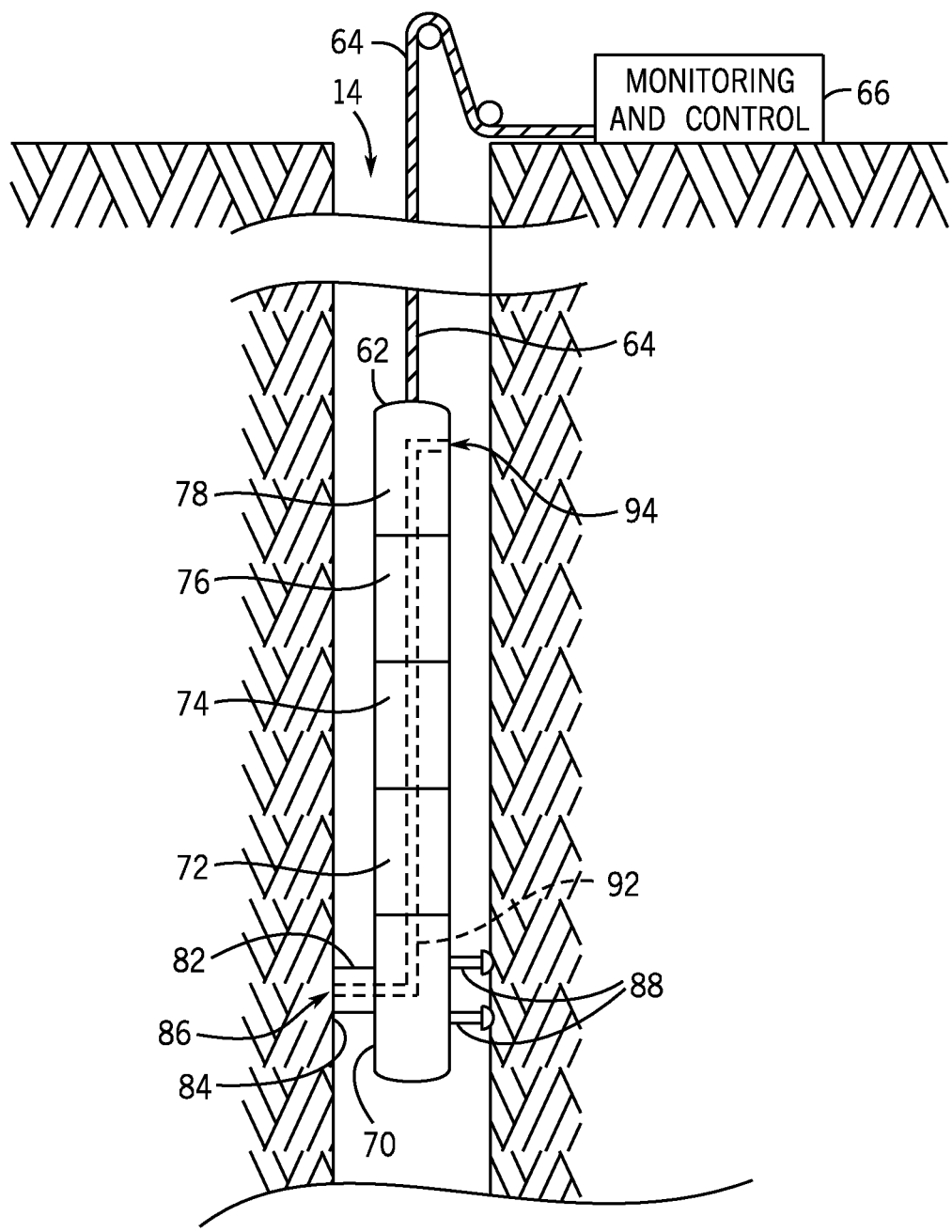
FIG. 2 generally depicts a fluid sampling tool deployed within a well on a wireline in accordance with an embodiment of the present disclosure.

Another example of using a downhole tool for formation testing within the well 14 is depicted in FIG. 2. In this embodiment, a fluid sampling tool 62 can be suspended in the well 14 on a cable 64. The cable 64 may be a wireline cable with at least one conductor that enables data transmission between the fluid sampling tool 62 and a monitoring and control system 66. The cable 64 may be raised and lowered within the well 14 in any suitable manner. For instance, the cable 64 can be reeled from a drum in a service truck, which may be a logging truck having the monitoring and control system 66. The monitoring and control system 66 can control movement of the fluid sampling tool 62 within the well 14 and can receive data from the fluid sampling tool 62. In a similar fashion to the monitoring and control system 56 of FIG. 1, the monitoring and control system 66 may include one or more computer systems or devices and may be a distributed computing system. The received data can be stored, communicated to an operator, or processed, for instance. While the fluid sampling tool 62 is here depicted as being deployed by way of a wireline, in some embodiments the fluid sampling tool 62 (or at least its functionality) can be incorporated into or as one or more modules of the bottomhole assembly 18, such as the LWD module 44 or the additional module 48.

The fluid sampling tool 62 can take various forms. While it is depicted in FIG. 2 as having a body including a probe module 70, a fluid analysis module 72, a pump module 74, a power module 76, and a fluid storage module 78, the fluid sampling tool 62 may include different modules in other embodiments. The probe module 70 can include a probe 82 that may be extended (e.g., hydraulically driven) and pressed into engagement against a wall 84 of the well 14 to draw fluid from a formation into the fluid sampling tool 62 through an intake 86. As depicted, the probe module 70 can also include one or more setting pistons 88 that may be extended outwardly to engage the wall 84 and push the end face of the probe 82 against another portion of the wall 84. In some embodiments, the probe 82 can include a sealing element or packer that isolates the intake 86 from the rest of the wellbore. In other embodiments, the fluid sampling tool 62 could include one or more inflatable packers that can be extended from the body of the fluid sampling tool 62 to circumferentially engage the wall 84 and isolate a region of the well 14 near the intake 86 from the rest of the wellbore. In such embodiments, the extendable probe 82 and setting pistons 88 could be omitted and the intake 86 could be provided in the body of the fluid sampling tool 62, such as in the body of a packer module housing an extendable packer.

The pump module 74 can draw the sampled formation fluid into the intake 86, through a flowline 92, and then either out into the wellbore through an outlet 94 or into a storage container (e.g., a bottle within fluid storage module 78) for transport back to the surface when the fluid sampling tool 62 is removed from the well 14. The fluid analysis module 72, which may also be referred to as the fluid analyzer 72 or a DFA module, can include one or more sensors for measuring properties of the sampled formation fluid, such as the optical density of the fluid, and the power module 76 provides power to electronic components of the fluid sampling tool 62. In some embodiments, the fluid analysis module 72 may include a downhole pressure-volume-temperature PVT unit and may obtain microfluidic measurements. In such embodiments, the fluid analysis module 72 may be referred to as a DFA microfluidics module. The measurements may be utilized to estimate a formation volume factor of the contaminated formation fluid, as well as density, optical density, GOR, compressibility, saturation pressure, viscosity, and/or mass fractions of compositional components of the contaminated formation fluid and/or contaminants therein (e.g., OBM filtrate), among others.

The drilling and wireline environments depicted in FIGS. 1 and 2 are examples of environments in which a fluid sampling tool may be used to facilitate analysis of a downhole fluid. The presently disclosed techniques, however, could be implemented in other environments as well. For instance, the fluid sampling tool 62 may be deployed in other manners, such as by a slickline, coiled tubing, or a pipe string.

Figure 3:
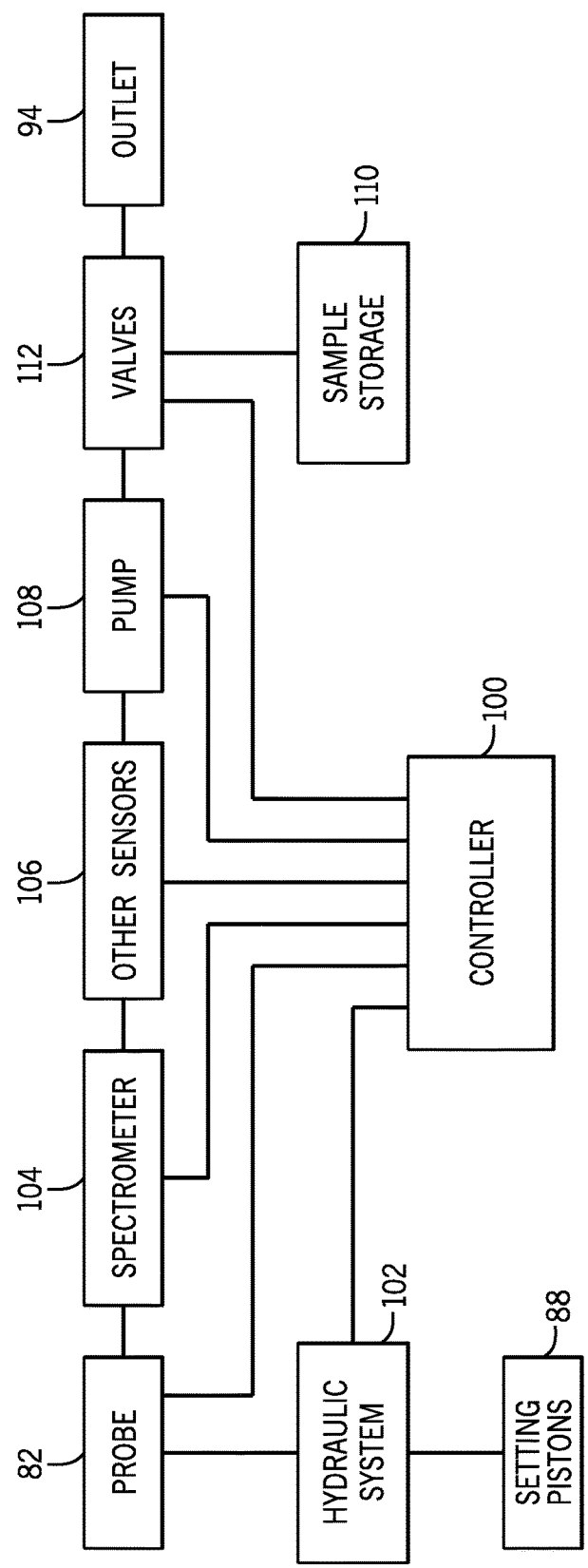
FIG. 3 is a block diagram of components of a fluid sampling tool operated by a controller in accordance with an embodiment of the present disclosure.

Additional details as to the construction and operation of the fluid sampling tool 62 may be better understood through reference to FIG. 3. As shown in this figure, various components for carrying out functions of the fluid sampling tool 62 can be connected to a controller 100. The various components can include a hydraulic system 102 connected to the probe 82 and the setting pistons 88, a spectrometer 104 for measuring fluid optical properties, one or more other sensors 106, a pump 108, and valves 112 for diverting sampled fluid into storage devices 110 rather than venting it through the outlet 94. The controller 100 may include or be coupled to an operator interface (not shown) that provides logs of predicted formation fluid properties that are accessible to an operator.

In operation, the hydraulic system 102 can extend the probe 82 and the setting pistons 88 to facilitate sampling of a formation fluid through the wall 84 of the well 14. It also can retract the probe 82 and the setting pistons 88 to facilitate subsequent movement of the fluid sampling tool 62 within the well. The spectrometer 104, which can be positioned within the fluid analyzer 72, can collect data about optical properties of the sampled formation fluid. Such measured optical properties can include optical densities (absorbance) of the sampled formation fluid at different wavelengths of electromagnetic radiation. Using the optical densities, the composition of a sampled fluid (e.g., volume fractions of its constituent components) can be determined. Other sensors 106 can be provided in the fluid sampling tool 62 (e.g., as part of the probe module 70 or the fluid analyzer 72) to take additional measurements related to the sampled fluid. In various embodiments, these additional measurements could include reservoir pressure and temperature, live fluid density, live fluid viscosity, electrical resistivity, saturation pressure, and fluorescence, to name several examples. In some embodiments, as mentioned above, some or all of other sensors 106 may be incorporated into a DFA module (e.g., such as in a PVT unit) of the fluid sampling tool 62. Other characteristics, such as gas-to-oil ratio (GOR), may also be determined using the DFA measurements.

Any suitable pump 108 may be provided in the pump module 74 to enable formation fluid to be drawn into and pumped through the flowline 92 in the manner discussed above. Storage devices 110 for formation fluid samples can include any suitable vessels (e.g., bottles) for retaining and transporting desired samples within the fluid sampling tool 62 to the surface. Both the storage devices 110 and the valves 112 may be provided as part of the fluid storage module 78.

In the embodiment depicted in FIG. 3, the controller 100 can facilitate operation of the fluid sampling tool 62 by controlling various components. Specifically, the controller 100 can direct operation (e.g., by sending command signals) of the hydraulic system 102 to extend and retract the probe 82 and the setting pistons 88 and of the pump 108 to draw formation fluid samples into and through the fluid sampling tool. The controller 100 can also receive data from the spectrometer 104 and the other sensors 106. This data can be stored by the controller 100 or communicated to another system (e.g., the monitoring and control system 56 or 66) for analysis. In some embodiments, the controller 100 is itself capable of analyzing the data it receives from the spectrometer 104 and the other sensors 106. The controller 100 can also operate the valves 112 to divert sampled fluids from the flowline 92 into the storage devices 110.

The various fluid properties mentioned above and measured by the tools described herein may be affected by OBM filtrate contamination in the sampled fluid (referred to as "contaminated" fluid). For example, measured saturation pressures, such as measured by a downhole PVT unit of a DFA module, may be affected by OBM filtrate contamination and may not accurately reflect the saturation pressure of the uncontaminated fluid. The saturation pressures may increase or decrease with an increase in OBM filtrate contamination.

By way of example, FIGS. 4-6 depict plots of saturation pressure vs. OBM filtrate contamination (as a volume fraction expressed as percentage) data points indicating a relationship between saturation pressures, such as bubble point pressure or dew point pressure, and OBM filtrate contamination. FIG. 4 depicts a plot 400 of the bubble point pressure of heavy oil vs. volume fraction of various OBM filtrate contaminates (esters, mineral oil, and olefins). FIG. 5 depicts a plot 500 of measured bubble point pressure of black oil vs. volume fraction of various OBM filtrate contaminates (esters, mineral oil, and olefins). Similarly, FIG. 6 depicts a plot 600 of measured dew point pressure of gas condensate vs. volume fractions of various OBM filtrate contaminates (esters, mineral oil, and olefins). As shown in FIGS. 4-6, for an OBM filtrate contamination below a certain amount, the bubble point and dew point pressures are approximately a linear function of the OBM filtrate contamination, regardless of whether the bubble point and dew point increase or decrease relative to increased OBM filtrate contamination. In some embodiments, as shown in FIGS. 4-6, a linear function may be used to approximate the relationship between saturation pressure and OBM filtrate contaminations below about 40% volume. However, it should be appreciated that the slope of each linear approximation function varies with the composition of the OBM filtrate and the composition of the fluid. Thus, in other embodiments, a linear function may be used to approximate the relationship between saturation pressure and OBM filtrate contaminations about 10% volume or less, 20% volume or less, 30% volume or less, 40% volume or less, or other suitable OBM contamination obtained from saturation pressure and OBM filtrate contamination data.

In view of the linear function approximations discussed above, the saturation pressure of a contaminated fluid may be expressed as follows by Equation 1:

$$P^{sat} = v_{obm} P_{obm}^{hypo} + (1 - v_{obm}) P_0^{sat} \quad (1)$$

Where, $P^{sat}$ is the saturation pressure of the contaminated fluid, $v_{obm}$, is the OBM filtrate contamination in volume fraction of the contaminated fluid as measured by a downhole tool, $P_0^{sat}$ is the saturation pressure of the uncontaminated (also referred to as "native") fluid, and $P_{obm}^{hypo}$ is the hypothetical OBM filtrate saturation pressure. The hypothetical OBM filtrate saturation pressure may be used instead of the real OBM filtrate saturation pressure; because no gas is dissolved and the OBM filtrate is typically heavier than $C_7$, the real OBM filtrate saturation pressure is nearly zero. Additionally, using the hypothetical OBM filtrate saturation enables use of a linear function over a linear range of contamination, as the relationship of saturation pressure to OBM filtrate contamination may be non-linear at higher contamination.

By factoring $v_{obm}$, Equation 1 may be rewritten as Equation 2 below:

$$P^{sat} = (P_{obm}^{hypo} - P_O^{sat}) v_{obm} + P_O^{sat} \quad (2)$$

As mentioned, at relatively low OBM filtrate contamination, the saturation pressure is a linear function of OBM filtrate contamination. The slope of the line of such a linear function is $P_{obm}^{hypo} - P_0^{sat}$ and the y-axis intercept at a value of zero OBM filtrate concentration is $P_0^{sat}$. Thus, as described herein, saturation pressures may be measured during cleanup at different OBM filtrate contamination levels and the linear relationship may be approximated by Equation 2 and used to obtain the $P_0^{sat}$ of the uncontaminated fluid.

Figure 7:
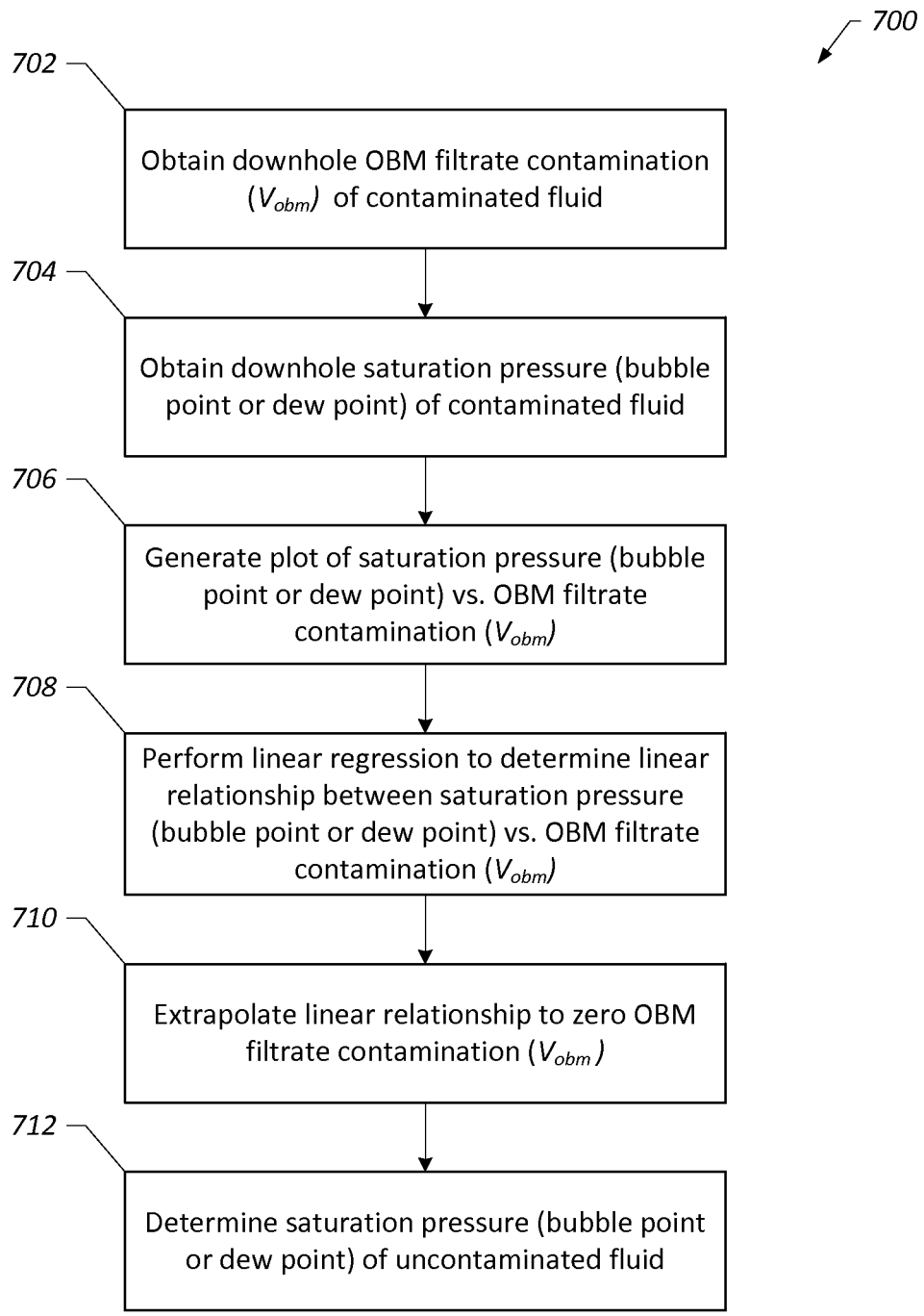
FIG. 7 is a block diagram of a process for determining saturation pressure of an uncontaminated fluid in accordance with an embodiment of the present disclosure.

FIG. 7 depicts a process for determining the saturation pressure (bubble point pressure or dew point pressure) of an uncontaminated fluid in accordance with the techniques described herein. The process may be performed using a downhole tool having a DFA module, such as that described above. As will be appreciated, the determination described in process 700 is executed on a downhole fluid sample, thus eliminating the need to preserve fluid samples and transport samples to the surface and, in some instances, to a laboratory for further analysis. The downhole fluid sample may be obtained by initiating a pumpout of contaminated fluid, such as during cleanup of a well.

Downhole OBM filtrate contamination ($v_{obm}$) may be obtained (block 702) by various suitable techniques. In some embodiments, properties such as optical density, gas/oil ratio, mass density, pumpout volume, pumpout time, and the like may be measured during pumpout and cleanout using a DFA apparatus. In such embodiments, OBM filtrate concentration may be determined by DFA OBM filtrate concentration (OCM) techniques, such as those described in U.S. Pat. Nos. 6,956,204 and 8,204,125. In some embodiments, the OBM filtrate concentration may be determined according to the techniques described in U.S. application Ser. No. 14/085,589, entitled "Method and Apparatus for Consistent and Robust Fitting in Oil-Based Mud Filtrate Contamination Monitoring for Multiple Downhole Sensors", now U.S. Pub. Ser. No. 2015/0142317, a copy of which is herein incorporated by reference. Next, downhole saturation pressure measurements of the contaminated fluid may be obtained (block 704). In some embodiments, downhole saturation pressure measurements may be obtained using a downhole PVT unit of a DFA module.

In some embodiments, the additional operations of process 700 may be performed after a threshold OBM filtrate contamination is reached. In such embodiments, OBM filtrate contamination may be continuously determined during pumpout of the contaminated fluid until sufficient fluid has been pumped to reach a desired OBM filtrate contamination. For example, in some embodiments the additional operations of the process 700 may be performed after a threshold OBM filtrate contamination of about 10% volume or less, 20% volume or less, 30% volume or less, 40% volume or less, or other suitable OBM contamination volume.

Next, a plot of the measured downhole saturation pressures vs. OBM filtrate contamination may be generated (block 706). As discussed above, in some embodiments the bubble point pressure or the dew point pressure may be plotted against the determined volume fraction of OBM filtrate contamination. Next, a linear regression may be performed on the data points of the plot to determine the linear relationship between the measured saturation pressures and the OBM filtrate contamination (block 708). As discussed above, the linear relationship may be expressed according to Equation 2 and the slope of the linear function may be $P_{obm}^{hypo} - P_O^{sat}$.

Next, the linear relationship may be extrapolated to a zero OBM filtrate contamination (block 710), e.g., a y-axis intercept, and the saturation pressure (bubble point pressure or dew point pressure) of the uncontaminated fluid may be determined (block 712). As will be appreciated, the process 700 described above may be performed for bubble point pressures or dew point pressures measured downhole.

Although the embodiments described above discuss determination of a linear relationship between saturation pressure and OBM filtrate contamination for certain volume fractions of OBM filtrate contamination, it should be appreciated that the linear relationship and linear function are provided by way of example and other embodiments may include a non-linear relationship. For example, some fluids and OBM mixtures may exhibit a non-linear relationship between saturation pressure and OBM filtrate contamination. In such embodiments, a polynomial or other non-linear function may be determined from a plot of saturation pressure vs. OBM filtrate contamination volume fraction, and the process 700 described above may be performed using a non-linear function instead of the linear function. Thus, in the manner described above, the non-linear function may be extrapolated to zero OBM filtrate to determine the saturation pressure of the uncontaminated fluid.

Figure 8:
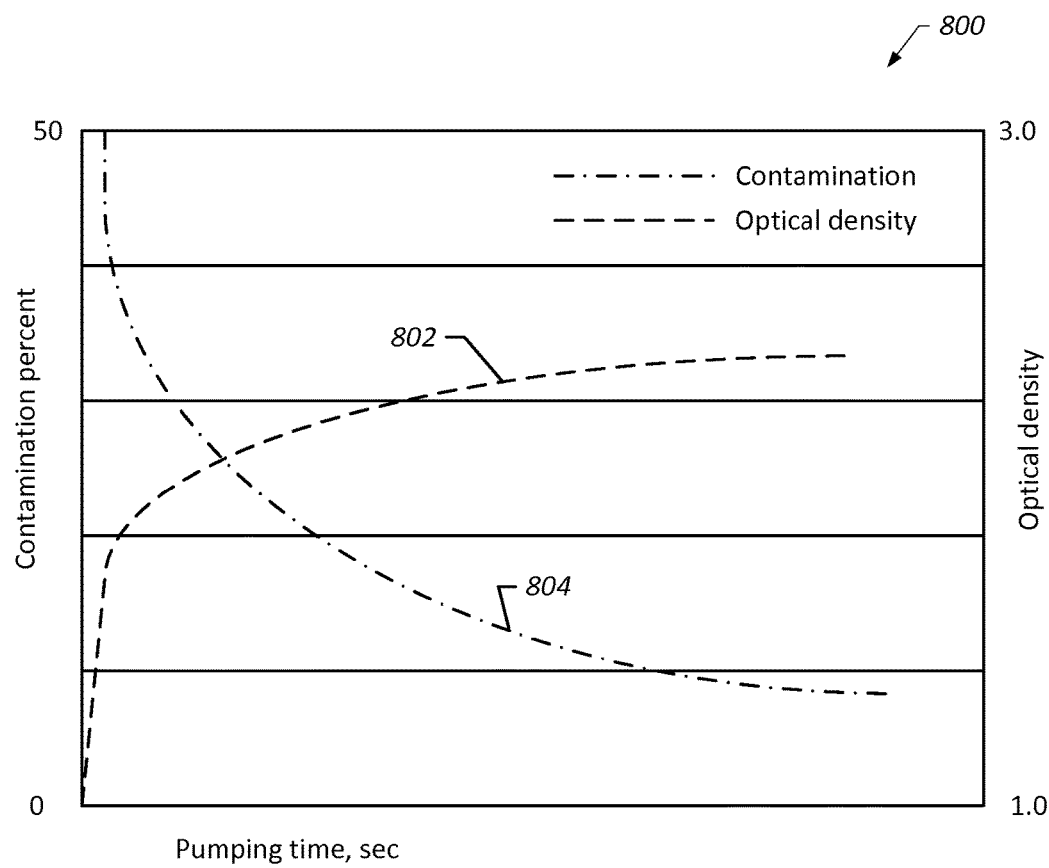
FIG. 8 is a plot of optical density and OBM filtrate contamination vs. pumping time in accordance with an embodiment of the present disclosure.
Figure 9:
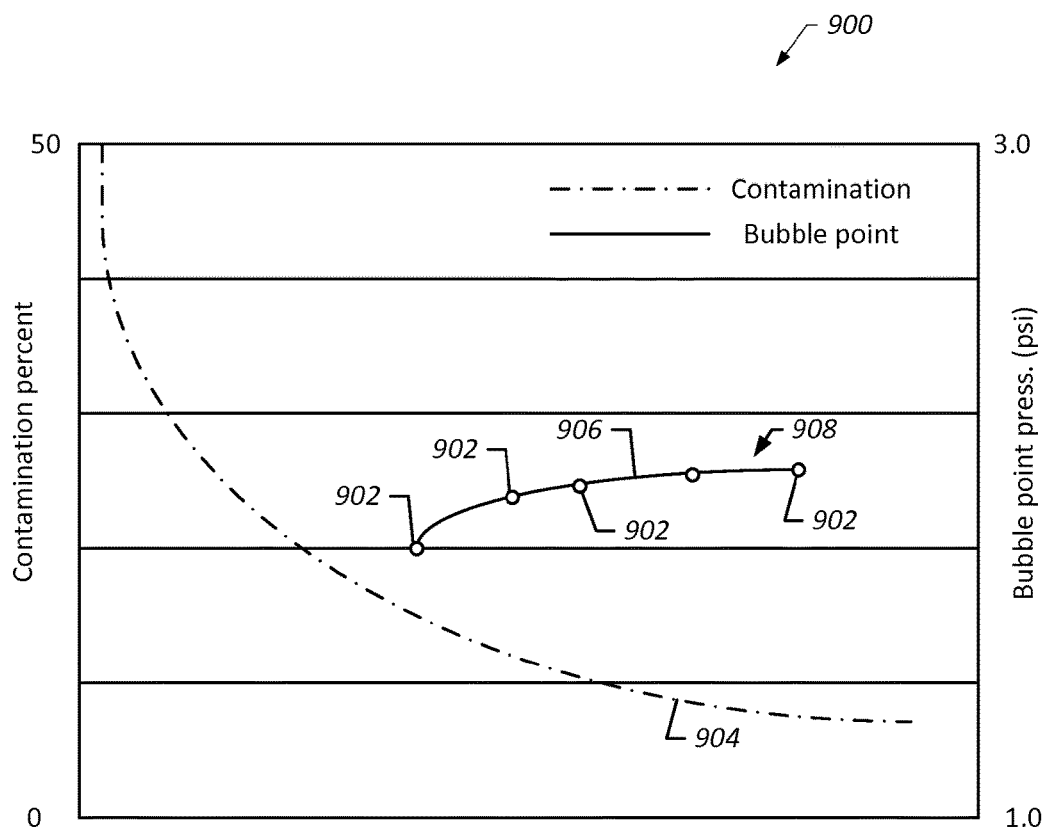
FIG. 9 is plot of measured bubble point pressures and OBM filtrate contamination vs. pumping time in accordance with an embodiment of the present disclosure.
Figure 10:
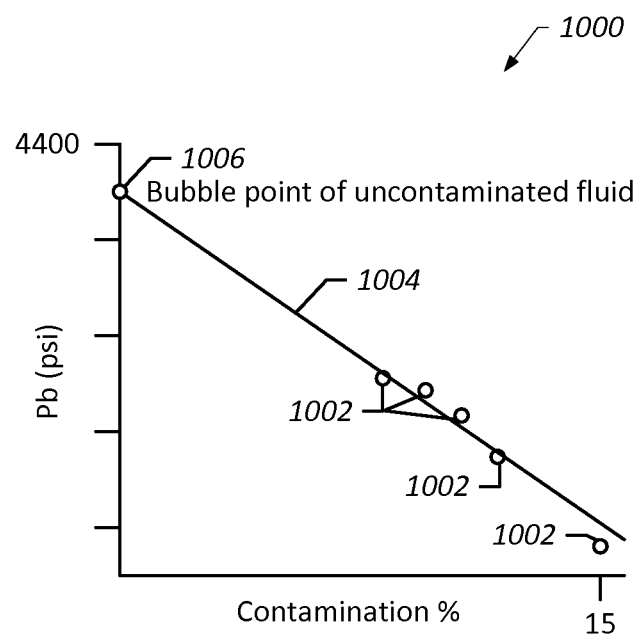
FIG. 10 is a plot of a linear function for measured bubble point pressures vs. OBM filtrate contamination in accordance with an embodiment of the present disclosure.

FIGS. 8-10 depict different plots illustrating an example of the techniques described above for determining saturation pressure of an uncontaminated fluid. FIG. 8 depicts a plot 800 of optical density (as measured using a DFA module) 802 and OBM filtrate contamination 804 as a function of pumping time during a downhole cleanup process for crude oil. As shown in the plot 800, the optical density decreases 802 with time. After the OBM filtrate contamination reaches a certain level, downhole saturation pressures may begin to be measured using, for example, a DFA module. FIG. 9 depicts a plot 900 of measured bubble point pressures 902 and OBM filtrate contamination 904 as a function of pumping time. As shown in FIG. 9, the bubble point pressure increases as the pumping time increases; however, the bubble point pressure curve 906 begins to flatten out as the pumping time increases, as illustrated by portion 908.

FIG. 10 depicts a plot 1000 of data points 1002 of measured bubble point pressure vs. OBM filtrate contamination, such as described above in block 708. As shown in FIG. 8, a linear regression may be used to determine a linear relationship (e.g., linear function 1004) for the data points 1002. As mentioned above, the slope of the line of the linear relationship 1004 may be $P_{obm}^{hypo} - P_O^{sat}$. The linear relationship 1004 may be extrapolated to zero OBM filtrate contamination, e.g., to intercept the y-axis of the plot 1000, as illustrated by point 1006 in FIG. 10. The bubble point pressure of the uncontaminated fluid may be determined at point 1006 (e.g., approximately 4375 psi).

In some embodiments, the flatness of the saturation pressure curve may be used as indication of OBM filtrate contamination. For example, as depicted in FIG. 8, as pumping time increases, the bubble point pressure curve 906 flattens out, as shown by portion 908. If the bubble point pressure curve 906 is flat (or its derivative is zero), the OBM filtrate contamination may be equal to or nearly zero.

In some embodiments, the OBM filtrate contamination may be determined using an observed bubble point pressure curve during a pumpout. Equation 1 described above may be rewritten to determine OBM filtrate contamination, as expressed below in Equation 3:

$$v_{obm} = \alpha \frac{P_0^{sat} - P^{sat}}{P_0^{sat} - P_{obm}^{hypo}} \quad (3)$$

Where $P^{sat}$ is the saturation pressure of the contaminated fluid as measured downhole (e.g., via a DFA apparatus), $P_{obm}^{hypo}$ is the hypothetical OBM saturation pressure and may be assumed to be equal to zero for crude oil or, in some embodiments, may be an adjusted parameter based on the fluid and OBM filtrate, $P_O^{sat}$ is the saturation pressure of the uncontaminated fluid, and α is a constant that depends on the properties of the OBM filtrate and the reservoir fluid. In some embodiments, α may be assumed to 1. In other embodiments, α may be determined from another fluid property that follows a lever rule, such as density. For example, in such embodiments, α may be calculated from the volume contamination from the density at two points and the relative contamination from the bubble point pressure at two points. The measured $P^{sat}$ may be fitted using the power function described below in Equation 4:

$$P^{sat} = P_0^{sat} - \beta v^{-\gamma} \quad (4)$$

Where V is the measured pumpout volume (e.g., as measured by a DFA module) and $P_O^{sat}$, β and γ, are adjustable parameters. In some embodiments, the power function described in Equation 4 may be expressed using the pumpout time t to replace the measured pumpout volume V. In other embodiments, other function for the saturation pressure may be fitted.

Figure 11:
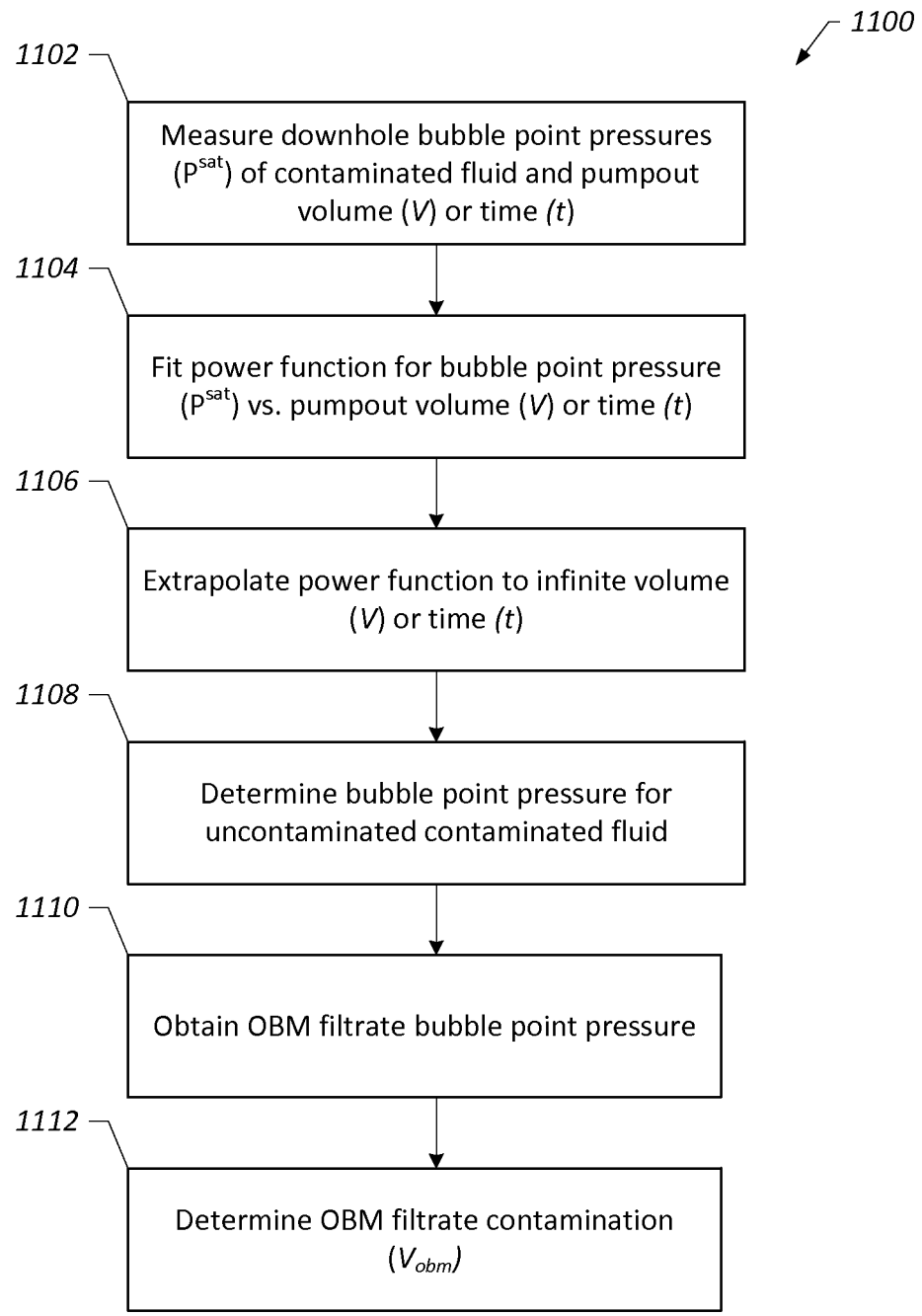
FIG. 11 is a block diagram of a process for determining OBM filtrate contamination from measured bubble point pressures in accordance with an embodiment of the present disclosure.

FIG. 11 depicts a process 1100 for determining OBM filtrate contamination based on measured downhole bubble point pressures in accordance with an embodiment of the present technique. The process may be performed using a downhole tool having a DFA module, such as the tools described above. As will be appreciated, the determination described in process 1100 is executed on a downhole fluid sample, thus eliminating the need to preserve fluid samples and transport samples to the surface and, in some instances, to a laboratory for further analysis.

Initially, downhole bubble point pressures of a fluid and pumpout volume or time may be measured (block 1102) during pumpout of contaminated fluid, such as during cleanup of a well. Next, the power function for bubble point pressure as a function of pumpout volume, as described by Equation 4, may be fitted to the measured bubble point pressure curve (block 1104). In other embodiments, as mentioned above, the pumpout time t may be used instead of the pumpout volume V and a corresponding power function of bubble point pressure as a function of pumpout time t may be fitted.

Next, the fitted power function may be extrapolated to infinite volume V, or, in some embodiments, infinite time t (block 1106), and the bubble point pressure for the uncontaminated fluid may be determined from the bubble point pressure at infinite volume V or infinite time t (block 1108). As described above, the OBM filtrate bubble point pressure may be obtained (block 1111). In some embodiments, the OBM filtrate bubble point pressure may be assumed to equal zero. In other embodiments, the OBM filtrate bubble point pressure may be obtained by fitting data obtained from another source, such as another well using the OBM filtrate. In other embodiments, the OBM filtrate bubble point pressure may be the hypothetical OBM filtrate saturation pressure, as described. Next, the OBM filtrate contamination may be determined using Equation 3 (block 1112). In some embodiments, the OBM filtrate contamination may be monitored to obtain a desired sample of the fluid in a downhole tool.

Figure 12:
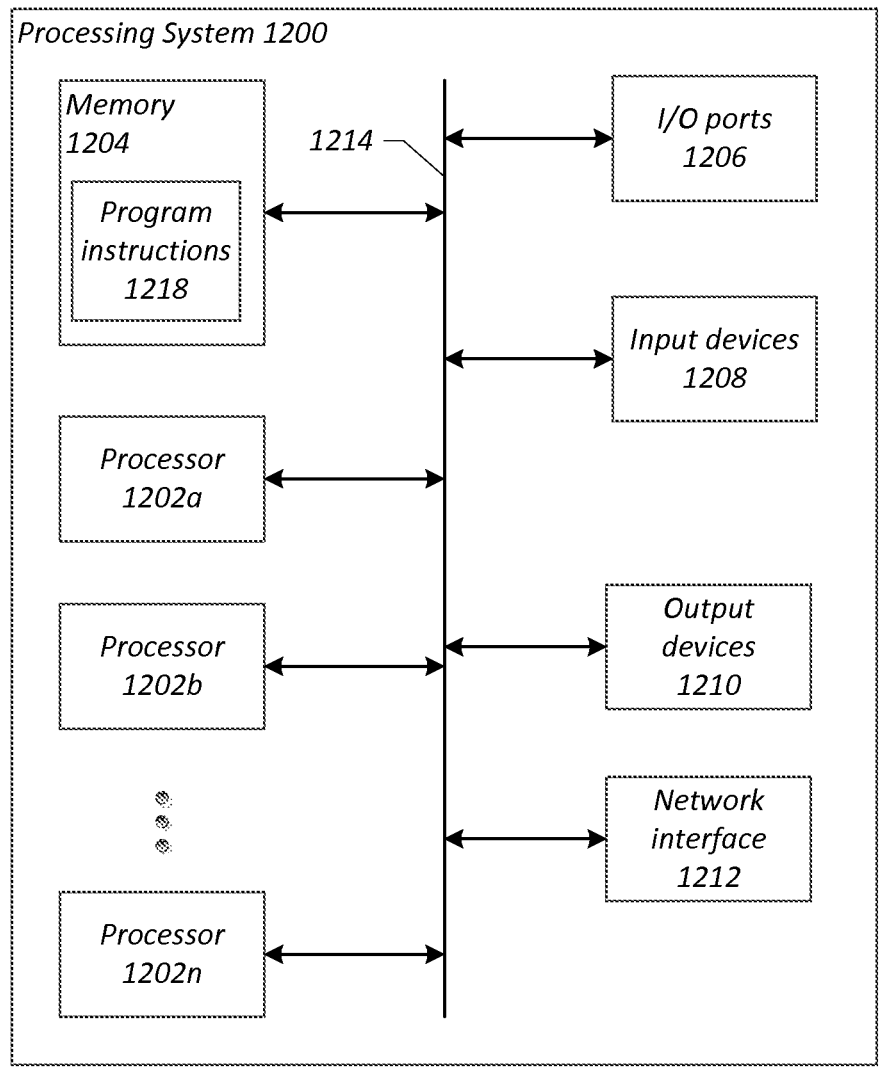
FIG. 12 is a block diagram of a processing system in accordance with an embodiment of the present disclosure.

FIG. 12 is a block diagram of an example processing system 1200 that may execute example machine-readable instructions used to implement one or more of processes described herein and, in some embodiments, to implement a portion of one or more of the example downhole tools described herein. The processing system 1000 may be or include, for example, controllers (e.g., controller 100), special-purpose computing devices, servers, personal computers, personal digital assistant (PDA) devices, tablet computers, wearable computing devices, smartphones, internet appliances, and/or other types of computing devices. Moreover, while it is possible that the entirety of the system 1200 shown in FIG. 17 is implemented within a downhole tool, it is also contemplated that one or more components or functions of the system 1200 may be implemented in wellsite surface equipment. As shown in the embodiment illustrated in FIG. 12, the processing system 1200 may include one or more processors (e.g., processors 1202A-1202N), a memory 1204, I/O ports 1206 input devices 1208, output devices 1210, and a network interface 1214. The process system 1200 may also include one or more additional interfaces 1214 to facilitate communication between the various components of the system 1200.

The processor 1202 may provide the processing capability to execute programs, user interfaces, and other functions of the system 1200. The processor 1202 may include one or more processors and may include "general-purpose" microprocessors, special purpose microprocessors, such as application-specific integrated circuits (ASICs), or any combination thereof. In some embodiments, the processor 1202 may include one or more reduced instruction set (RISC) processors, such as those implementing the Advanced RISC Machine (ARM) instruction set. Additionally, the processor 1202 may include single-core processors and multicore processors and may include graphics processors, video processors, and related chip sets. Accordingly, the system 1200 may be a uni-processor system having one processor (e.g., processor 1202a), or a multi-processor system having two or more suitable processors (e.g., 1202A-1202N). Multiple processors may be employed to provide for parallel or sequential execution of the techniques described herein. Processes, such as logic flows, described herein may be performed by the processor 1202 executing one or more computer programs to perform functions by operating on input data and generating corresponding output. The processor 1202 may receive instructions and data from a memory (e.g., memory 1204).

The memory 1204 (which may include one or more tangible non-transitory computer readable storage mediums) may include volatile memory and non-volatile memory accessible by the processor 1202 and other components of the system 1200. For example, the memory 1204 may include volatile memory, such as random access memory (RAM). The memory 1204 may also include non-volatile memory, such as ROM, flash memory, a hard drive, other suitable optical, magnetic, or solid-state storage mediums or any combination thereof. The memory 1204 may store a variety of information and may be used for a variety of purposes. For example, the memory 1204 may store executable computer code, such as the firmware for the system 1200, an operating system for the system 1200, and any other programs or other executable code for providing functions of the system 1200. Such executable computer code may include program instructions 1218 executable by a processor (e.g., one or more of processors 1202A-1202N) to implement one or more embodiments of the present disclosure. Program instructions 1218 may include computer program instructions for implementing one or more techniques described herein. Program instructions 1218 may include a computer program (which in certain forms is known as a program, software, software application, script, or code).

The interface 1214 may include multiple interfaces and may enable communication between various components of the system 1200, the processor 1202, and the memory 1204. In some embodiments, the interface 1214, the processor 1202, memory 1204, and one or more other components of the system 1200 may be implemented on a single chip, such as a system-on-a-chip (SOC). In other embodiments, these components, their functionalities, or both may be implemented on separate chips. The interface 1214 may enable communication between processors 1202a-1202n, the memory 1204, the network interface 1210, or any other devices of the system 1200 or a combination thereof. The interface 1214 may implement any suitable types of interfaces, such as Peripheral Component Interconnect (PCI) interfaces, the Universal Serial Bus (USB) interfaces, Thunderbolt interfaces, Firewire (IEEE-1394) interfaces, and so on.

The system 1200 may also include an input and output port 1208 to enable connection of additional devices, such as I/O devices 1214. Embodiments of the present disclosure may include any number of input and output ports 1208, including headphone and headset jacks, universal serial bus (USB) ports, Firewire (IEEE-1394) ports, Thunderbolt ports, and AC and DC power connectors. Further, the system 1200 may use the input and output ports to connect to and send or receive data with any other device, such as other portable computers, personal computers, printers, etc.

The processing system 1200 may include one or more input devices 1208. The input device(s) 1208 permit a user to enter data and commands used and executed by the processor 1212. The input device 1208 may include, for example, a keyboard, a mouse, a touchscreen, a track-pad, a trackball, an isopoint, and/or a voice recognition system, among others. The processing system 1200 may also include one or more output devices 1210. The output devices 1210 may include, for example, display devices (e.g., a liquid crystal display or cathode ray tube display (CRT), among others), printers, and/or speakers, among others.

The system 1200 depicted in FIG. 12 also includes a network interface 1210. The network interface 1210 may include a wired network interface card (NIC), a wireless (e.g., radio frequency) network interface card, or combination thereof. The network interface 1210 may include known circuitry for receiving and sending signals to and from communications networks, such as an antenna system, an RF transceiver, an amplifier, a tuner, an oscillator, a digital signal processor, a modem, a subscriber identity module (SIM) card, memory, and so forth. The network interface 1210 may communicate with networks (e.g., network 1216), such as the Internet, an intranet, a cellular telephone network, a wide area network (WAN), a local area network (LAN), a metropolitan area network (MAN), or other devices by wired or wireless communication using any suitable communications standard, protocol, or technology.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language is not generally intended to imply that features, elements, and/or operations are in any way used for one or more implementations or that one or more implementations necessarily include logic for deciding, with or without user input or prompting, whether these features, elements, and/or operations are included or are to be performed in any particular implementation.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims. Although specific terms are employed herein, they are used in a generic and descriptive sense and not for purposes of limitation.

What is claimed is:

1. A method, comprising:
   initiating a pumpout process of downhole tool positioned in a wellbore;
   providing a controller with at least one property of a first fluid measured downhole by the downhole tool, oil-based mud (OBM) filtrate contamination of the first fluid, wherein the first fluid comprises a formation fluid and OBM filtrate;
   providing with the controller with downhole saturation pressure measurements of the first fluid measured downhole by the downhole tool;
   in the controller, continuously determining a relationship between the downhole saturation pressure measurements and the OBM filtrate contamination;
   when the relationship is determined, extrapolating, in the controller, the determined relationship between the downhole saturation pressure measurements and the OBM filtrate contamination to a zero OBM filtrate contamination to obtain a saturation pressure of the formation fluid at the zero OBM filtrate contamination.

2. The method of claim 1, wherein the downhole saturation pressure measurements comprise bubble point measurements and the saturation pressure of the formation fluid is a bubble point pressure of the formation fluid.

3. The method of claim 1, wherein determining a relationship between the downhole saturation pressure measurements and the downhole OBM filtrate contamination comprises:
   generating a plot of the downhole saturation pressure measurements versus the downhole OBM filtrate contamination; and
   performing a linear regression to determine a linear function between the downhole saturation pressure measurements and the downhole OBM filtrate contamination.

4. The method of claim 3, wherein extrapolating the determined relationship between the downhole saturation pressure measurements and the OBM filtrate contamination to a zero OBM filtrate contamination comprises extrapolating the linear function to a zero OBM filtrate contamination.

5. The method of claim 1, wherein the at least one property comprises an optical density, a gas/oil ratio, a mass density, a pressure gradient, a pumpout volume, or a pumpout time.

6. The method of claim 1, determining a relationship between the downhole saturation pressure measurements and the OBM filtrate contamination comprises determining a threshold level of OBM filtrate contamination.

\* \* \* \* \*